(12) United States Patent
Sunley

(10) Patent No.: US 10,207,260 B2
(45) Date of Patent: Feb. 19, 2019

(54) CARBONYLATION CATALYST AND PROCESS

(71) Applicant: BP Chemicals Limited, Middlesex (GB)

(72) Inventor: John Glenn Sunley, East Yorkshire (GB)

(73) Assignee: BP Chemicals Limited, Sunbury on Thames (GB)

( * ) Notice: Subject to any disclaimer, the term of this patent is extended or adjusted under 35 U.S.C. 154(b) by 250 days.

(21) Appl. No.: 14/772,959

(22) PCT Filed: Mar. 6, 2014

(86) PCT No.: PCT/EP2014/054393
§ 371 (c)(1),
(2) Date: Sep. 4, 2015

(87) PCT Pub. No.: WO2014/135661
PCT Pub. Date: Sep. 12, 2014

(65) Prior Publication Data
US 2016/0016155 A1  Jan. 21, 2016

(30) Foreign Application Priority Data
Mar. 8, 2013  (EP) .................................. 13158470

(51) Int. Cl.
| | | |
|---|---|---|
| *C07C 67/37* | (2006.01) | |
| *C07C 51/12* | (2006.01) | |
| *B01J 29/87* | (2006.01) | |
| *C07C 51/347* | (2006.01) | |
| *C07C 51/09* | (2006.01) | |
| *C07C 53/08* | (2006.01) | |
| *C07C 29/132* | (2006.01) | |
| *C07C 29/153* | (2006.01) | |
| *C07C 29/136* | (2006.01) | |
| *B01J 29/06* | (2006.01) | |
| *B01J 29/18* | (2006.01) | |
| *B01J 29/24* | (2006.01) | |
| *B01J 29/65* | (2006.01) | |
| *B01J 29/70* | (2006.01) | |
| *B01J 35/10* | (2006.01) | |
| *B01J 37/00* | (2006.01) | |
| *C01B 39/26* | (2006.01) | |
| *C01B 39/06* | (2006.01) | |
| *C07C 69/14* | (2006.01) | |

(52) U.S. Cl.
CPC .............. *B01J 29/87* (2013.01); *B01J 29/06* (2013.01); *B01J 29/18* (2013.01); *B01J 29/185* (2013.01); *B01J 29/24* (2013.01); *B01J 29/65* (2013.01); *B01J 29/70* (2013.01); *B01J 29/7015* (2013.01); *B01J 29/7026* (2013.01); *B01J 35/1033* (2013.01); *B01J 35/1038* (2013.01); *B01J 37/0009* (2013.01); *C01B 39/065* (2013.01); *C01B 39/265* (2013.01); *C07C 29/132* (2013.01); *C07C 29/136* (2013.01); *C07C 29/153* (2013.01); *C07C 51/09* (2013.01); *C07C 51/12* (2013.01); *C07C 51/347* (2013.01); *C07C 53/08* (2013.01); *C07C 67/37* (2013.01); *B01J 2229/14* (2013.01); *B01J 2229/18* (2013.01); *B01J 2229/42* (2013.01); *C07C 69/14* (2013.01)

(58) Field of Classification Search
CPC ....... C07C 51/347; C07C 51/09; C07C 51/12; C07C 53/08; C07C 67/37; C07C 69/14; C07C 29/136; C07C 29/132; C07C 29/153
USPC .................................. 562/519; 560/232, 241
See application file for complete search history.

(56) References Cited

U.S. PATENT DOCUMENTS

| 7,465,822 | B2 | 12/2008 | Cheung et al. | |
|---|---|---|---|---|
| 2007/0238897 | A1 | 10/2007 | Cheung et al. | |
| 2008/0091046 | A1* | 4/2008 | Smith | C07C 51/12 562/519 |
| 2008/0146833 | A1 | 6/2008 | Iglesia et al. | |
| 2010/0317900 | A1 | 12/2010 | Daniel et al. | |
| 2012/0053360 | A1* | 3/2012 | Ditzel | B01J 29/18 560/232 |
| 2012/0101298 | A1* | 4/2012 | Ditzel | B01J 29/18 560/206 |

FOREIGN PATENT DOCUMENTS

| CN | 101284673 A | 10/2008 |
|---|---|---|
| DE | 36 06169 A1 | 8/1987 |
| EA | 201001010 A1 | 2/2011 |
| EP | 1 101 735 A1 | 5/2001 |
| EP | 1 985 607 A1 | 10/2008 |
| EP | 2 251 082 A1 | 11/2010 |
| EP | 2 251 083 A1 | 11/2010 |
| RU | 2458909 A | 1/2011 |
| WO | WO 97/15528 A1 | 5/1997 |
| WO | WO 00/06492 A1 | 2/2000 |
| WO | WO 2005/105720 A1 | 11/2005 |

* cited by examiner

*Primary Examiner* — Elizabeth D Wood
(74) *Attorney, Agent, or Firm* — McDonnell Boehnen Hulbert & Berghoff LLP

(57) ABSTRACT

Carbonylation process for producing methyl acetate, by contacting dimethyl ether and carbon monoxide under carbonylation conditions in the presence of a catalyst having a zeolite of micropore volume of 0.01 ml/g. The zeolite is an as-synthesized organic structure directing agent-containing zeolite and contains at least one channel which is defined by an 8-member ring.

8 Claims, No Drawings

CARBONYLATION CATALYST AND PROCESS

This application is the U.S. national phase of International Application No. PCT/EP2014/054393 filed Mar. 6, 2014 which designated the U.S. and claims priority to European Patent Application No. 13158470.8 filed Mar. 8, 2013, the entire contents of each of which are hereby incorporated by reference.

This invention relates to zeolite catalysts and their use in processes for producing methyl acetate by the carbonylation of dimethyl ether with carbon monoxide.

Solid crystalline aluminosilicate zeolite catalysts have been known to be effective for the carbonylation of dimethyl ether with carbon monoxide to form methyl acetate. Zeolites occur naturally and may also be prepared synthetically. Synthetic zeolites include for example mordenite and ferrierite. Other components, such as boron or gallium, may be used to partially replace the aluminium or silicon in the zeolite framework structure.

In general, zeolites are prepared by a procedure which involves crystallising the zeolite structure from aqueous synthesis mixtures comprising sources of appropriate oxides, such as silica and alumina. Structure directing agents which influence the formation of channels or tunnel like structures within a zeolite may also be included in the synthesis mixture. Structure directing agents may be inorganic or organic. Typically, structure directing agents are removed from a resultant zeolite prior to its use as a catalyst. A variety of methods are known to remove structure directing agents, including by calcining at high temperature. Zeolite catalysts produced in this manner are described, for example in WO 2005/105720 and DE 3606169.

WO 2005/105720 describes a carbonylation process for the carbonylation of aliphatic alcohols and/or reactive derivatives thereof in the presence of a mordenite catalyst which has, in addition to aluminium and silicon, one or more gallium, boron and iron as framework elements and which catalyst is also loaded with copper, nickel, iridium, rhodium or cobalt. The preparation of gallium mordenite is described in which tetraethyl ammonium bromide is used as an organic template and which template is removed by calcining at 550° C. prior to use in the carbonylation of methanol with carbon monoxide.

DE 3606169 discloses a process for the preparation of acetic acid, methyl acetate and/or dimethyl ether by carbonylation of anhydrous methanol, methyl acetate and/or dimethyl ether in the presence of cobalt containing zeolites or zeolites mixed with cobalt salts. The carbonylation is optionally carried out in the presence of a halide. According to DE3606169 preferred zeolites are those of the pentasil type whose pore sizes are intermediate between that of zeolite A on the one hand and zeolites X and Y on the other and wherein prior to use in carbonylation the zeolites are calcined at 500° C.

U.S. Pat. No. 7,465,822 describes a process for the carbonylation of a lower alkyl ether with carbon monoxide in the presence of a zeolite catalyst. It is disclosed that in the synthesis of the zeolite, an organic structure directing agent may be included in the reaction mixture which mixture is subsequently crystallised and calcined at high temperatures.

An important aspect of any catalytic process is the activity and selectivity of a catalyst when exposed to the desired process conditions. The improvement of catalytic performance in carbonylation reactions is a continuous objective of process and catalyst development research. EP 2251082, for example describes a process whereby the carbonylation catalytic activity of mordenite is improved by treating a mordenite with an aqueous solution of ammonium hydroxide. WO 97/15528 describes a process for modifying the porosity of aluminosilicates whose porosity is not amenable to modification by acid extraction. The process involves contacting the aluminosilicate with an alkali aluminate and then extracting the aluminate-treated material with an extraction agent so as to form a porosity-modified aluminosilicate. Modifying the porosity of such aluminosilicates could improve their catalytic and adsorbent properties.

One problem with zeolite catalysts used in carbonylation processes, such as processes for the production of methyl acetate by carbonylating dimethyl ether with carbon monoxide, is the existence of an induction period, typically at start-up of the reaction, during which undesirable hydrocarbon materials may be generated in preference to carbonylation products. Depending on the nature of the catalyst and the reaction conditions employed, the induction period can last for a significant period of time. It is only subsequent to the induction period that the catalysts begin to be selective to desirable carbonylation products.

Thus, it would be highly desirable to provide a zeolite catalyst which eliminates or at least reduces the induction period in carbonylation processes, and in particular eliminates or at least reduces the induction period in processes for the production of methyl acetate by the carbonylation of dimethyl ether with carbon monoxide.

Applicant has now found that the induction period in processes for the carbonylation of dimethyl ether with carbon monoxide to produce methyl acetate can be shortened by utilising a zeolite catalyst which exhibits a micropore volume of 0.01 or less. This result is unexpected, since it had been previously believed that reducing the micropore volume of the zeolite would decrease its selectivity by restricting access of reactant molecules to the zeolite micropores.

Accordingly, the present invention provides a catalyst for the carbonylation of dimethyl ether with carbon monoxide to produce methyl acetate wherein the catalyst comprises a zeolite of micropore volume of 0.01 ml/g or less.

In one embodiment of the present invention, the zeolite is a zeolite of framework type MOR, and in particular is mordenite.

In another embodiment of the present invention, the zeolite is in an ion-exchanged form, for example an ion-exchanged form of mordenite.

In a further embodiment of the present invention, the zeolite is a mordenite in ammonium form or hydrogen form.

In a further embodiment of the present invention, the zeolite is a mordenite in ammonium form and the mordenite has the framework elements, silicon, aluminium and gallium.

The term "micropore" and "mesopore" as used herein follows the definition set forth by the International Union of Pure and Applied Chemistry (IUPAC), Division of Physical Chemistry in the Manual of Symbols and Terminology for Physicochemical Quantities and Units, Appendix II Definitions, Terminology and Symbols in Colloid and Surface Chemistry Part I, adopted by the IUPAC Council at Washington D.C., USA on 23 Jul. 1971. Pores with widths or diameters not exceeding 2.0 nanometers (20 Angstroms) are called "micropores". Pores with widths or diameters exceeding 2.0 nanometers but not exceeding 50 nanometers are called "mesopores"

The zeolite catalysts of the present invention are characterised by having a micropore volume of 0.01 ml/g or less, that is a micropore volume which is practically zero. In particular, the zeolite catalysts of the present invention exhibit a micropore volume of from 0.00 ml/g to 0.01 ml/g.

As used herein "micropore volume" is used to indicate the total volume of pores having a diameter not exceeding 2.0 nanometers as determined by the t-plot method using nitrogen adsorption at 77K. The t-plot method is described by Lippens B. C. and de Boer J. H (1965) Studies on pore systems in catalysts J Catalysis, 4, 319-323. The determination of micropore volume of zeolitic materials using the t-plot method is well known to those skilled in the art.

Zeolites are crystalline microporous aluminosilicates which have framework structures constructed from tetrahedra of $SiO_4$ and $AlO_4$ that share vertices. Each framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC. A description of zeolites, their structure, properties and methods of synthesis can be found in The *Atlas of Zeolite Framework Types* (C. Baerlocher, W. M. Meier, D. H. Olson, $5^{th}$ Ed. Elsevier, Amsterdam, 2001) in conjunction with the web-based version (http://www.iza-structure.org/databases/).

For use in carbonylation processes, for example carbonylation processes of dimethyl ether with carbon monoxide, a zeolite contains at least one channel or pocket (hereinafter referred to as 'channels') which is defined by an 8-member ring. Preferably, the 8-member ring channel is interconnected with at least one channel defined by a ring with 10 or 12 members. The window size of the zeolite channel systems should be such that the reactant dimethyl ether and carbon monoxide molecules can diffuse freely in and out of the zeolite framework. Suitably, the window size of an 8-member ring channel is at least 2.5×3.6 Angstroms.

In an embodiment of the present invention, the zeolite is selected from zeolites of a framework type selected from MOR, FER, OFF, CHA, GME and MFS.

Examples of zeolites of framework type MOR include mordenite. Examples of zeolites of framework type FER include ferrierite and ZSM-35. Examples of zeolites of framework type OFF include offretite. Examples of zeolites of framework type CHA include chabazite. Examples of zeolites of framework type GME include gmelinite. Examples of zeolites of framework type MFS include ZSM-57.

In addition to silicon and aluminium, the zeolite, such as mordenite may have as framework elements, trivalent metals, such as at least one of gallium, boron and iron, preferably gallium.

For the purposes of the present invention, the silica to alumina molar ratio of a zeolite is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value. The bulk silica to alumina molar ratio (herein also termed "SAR") of a zeolite may vary. For example, the SAR of a zeolite, such as mordenite, may range from as low as 5 to over 90. The SAR of the zeolites in the present invention may suitably be in the range from 10 to 90:1, for example 20 to 60:1, such as 20 to 40:1.

Zeolites are typically microporous which means that they possess pores having diameters of 2.0 nanometers or less. For the purposes of the present invention, a zeolite has a micropore volume of 0.01 ml/g or less.

Conveniently, zeolites having micropore volumes not exceeding 0.01 ml/g may be prepared by crystallising the zeolite from a synthesis mixture which comprises an organic structure directing agent.

A preferred procedure for preparing a zeolite having a micropore volume of from 0.00 ml/g to 0.01 ml/g comprises the following steps:
 (i) preparing the zeolite from a synthesis mixture which contains an organic structure directing agent;
 (ii) treating the as-synthesised zeolite with an aqueous solution of ammonium ions;
 (iii) drying the ammonium treated zeolite; and
wherein the organic structure directing agent is not removed or not substantially removed from the zeolite.

Once the zeolite has been synthesised, it can be composited with a binder material (binder) that provides additional hardness to the finished catalyst.

A preferred procedure for preparing a zeolite having a micropore volume of from 0.00 ml/g to 0.01 ml/g composited with a binder comprises the following steps:
 (i) preparing a zeolite from a synthesis mixture which contains an organic structure directing agent and which zeolite has a micropore volume of from 0.00 ml/g to 0.01 ml/g;
 (ii) compositing the zeolite prepared in step (i) with an inorganic oxide binder;
 (iii) extruding the composited zeolite to form the desired zeolite particles;
 (iv) calcining the extruded zeolite composite so as to maintain a zeolite micropore volume of 0.00 ml/g to 0.01 ml/g;
 (v) treating the calcined zeolite composite with an aqueous solution of ammonium ions; and
 (vi) drying the ammonium treated zeolite composite.

Zeolites, such as mordenites, having micropore volumes not exceeding 0.01 ml/g, as synthesised, may be prepared by crystallising the zeolite from a synthesis mixture comprising a source of silica, a source of alumina, a source of alkali or alkaline earth metal, water and an organic structure directing agent.

The sources of the silica, alumina and alkali or alkaline earth metal may be those conventionally used in zeolite synthesis. Representative of silica sources are colloidal silica, precipitated silica, silica gel, fumed silica and solid silica, silicon-containing compounds, such as silicic acid, metal silicates, such as sodium silicate and metallosilicates including aluminosilicates, for example sodium aluminosilicate.

The source of alumina may be provided by a variety of sources, including activated alumina, alumina trihydrate, gamma alumina, and water soluble aluminium salts, such as aluminium sulphate, aluminium nitrate, hydrated aluminium hydroxides and aluminates, such as sodium aluminate or other metal aluminates.

It will be understood that each of the silica and alumina utilised in the synthesis mixture for preparing the zeolite can be supplied by one or more initial reagents. For example, silica can be supplied by an aqueous solution of sodium hydroxide or an aqueous solution of sodium silicate.

The sources of the alkali or alkaline earth metal include alkali metal or alkaline metal salts readily soluble in water, such as sodium aluminate or sodium silicate or in the form of hydroxides, such as alkali metal hydroxides, preferably, sodium hydroxide If additional metals are desired to be present in the framework of the zeolite, such as trivalent metals selected from at least one of gallium, boron and iron they will generally be added to the synthesis mixture in the form of water soluble salts.

Conveniently, the zeolite may be prepared from a synthesis mixture which further comprises a source of gallium oxide ($Ga_2O_3$), such as gallium nitrate. In particular, a synthesis mixture comprising a source of gallium oxide may be used to prepare a mordenite containing gallium as a framework element.

The organic structure directing agent can be any organic compound capable of directing the construction of the zeolite structure and is suitably a basic nitrogen compound such as salts and bases of quaternary ammonium compounds such as salts and bases of aliphatic quaternary ammonium compounds and aromatic quaternary ammonium compounds. Suitable compounds include hydroxides and salts, such as halides, for example bromides.

Specific examples of aliphatic quaternary ammonium compounds include tetraalkylammonium compounds, for example tetraethylammonium compounds, tetraalkyl ammonium salts, such as tetraalkyl ammonium halides for example tetraethylammonium bromide and trialkylmethyl ammonium compounds, for example triethylmethylammonium bromide. Specific examples of aromatic quaternary ammonium compounds include phenyl or benzyl trialkyl ammonium compounds, for example benzyl trimethylammonium bromide or phenyl trimethylammonium bromide or phenyl or benzyl tetraalkyl ammonium compounds.

A preferred organic structure directing agent is tetraethylammonium bromide. However, other basic nitrogen compounds may be employed as a structure directing agent such as heterocyclic compounds possessing at least one amine functional group, for example morpholines, such as morpholine hydrobromide.

The components of the synthesis mixture can be added to water in any order.

In some or all embodiments of the present invention, a zeolite may be prepared from a synthesis mixture which comprises silica, for example fumed silica, a water soluble aluminate, for example sodium aluminate, an alkali metal hydroxide, for example sodium hydroxide, an organic structure directing agent, for example a quaternary ammonium compound, such as an aliphatic quaternary ammonium compound, for example a tetralkylammonium compound, in particular a tetraethylammonium compound and more particularly a tetralkylammonium halide, for example tetraethylammonium bromide, water and optionally a source of gallium oxide.

In order to maintain a predetermined composition in the zeolite it will generally be preferable to employ starting materials of known purity and composition so that composition control is maintained.

The components are brought together in defined proportions in water to compose a zeolite-forming aqueous synthesis mixture. The synthesis mixture is hydrothermally treated (with or without pressure) for a time and at a temperature to promote crystallisation.

Crystallisation can be carried out, with or without pressure, at either static or agitated conditions, for example stirred conditions, in a suitable reactor vessel, such as stainless steel autoclaves, at a temperature of about 80° C. to about 210° C. for a time sufficient for crystallisation to occur. Formation of the crystalline zeolite can take anywhere from around 30 minutes up to as long as several weeks. The duration depends on the temperature employed, with higher temperatures typically requiring shorter hydrothermal treatments.

Suitably, the synthesis mixture is maintained until crystals of the zeolite are formed, for example for a period of from 6 to 500 hours at elevated temperature and at a temperature, for example of 80° C. to 210° C.

In some or all embodiments of the present invention, the synthesis mixture is hydrothermally treated at atmospheric pressure with agitation, for example with stirring.

In some or all embodiments of the present invention, the synthesis mixture is hydrothermally treated at a temperature of from about 150° C. to about 170° C. for a period of about 80 hours to about 340 hours, optionally with agitation, for example with stirring, such as at a stirring speed of from about 200 rpm to about 550 rpm.

Typically, the crystalline zeolite is formed in solution and can be recovered by standard means, such as by centrifugation or filtration, washed with water, suitably with deionised or distilled water, and dried. The synthetic zeolite crystallises as a fine powder which exhibits an x-ray diffraction pattern characteristic of that particular type of zeolite.

The proportions of the components of the synthesis mixture can be adjusted to produce the desired zeolite. In the case of mordenite, the following molar ratios, expressed as oxide ratios, of synthesis mixture components may be employed:—

$SiO_2/M_2O_3$ from 10 to 100, preferably 20 to 60
$H_2O/Al_2O_3$ from 500 to 3000
$SDA/Al_2O_3$ from 1 to 15
$Na_2O/Al_2O_3$ from 1 to 10 wherein M is a trivalent metal selected from one or more of Al, Ga, B and Fe; SDA is the organic structure directing agent, suitably a basic nitrogen compound.

Suitably, a mordenite containing gallium as a framework element may be prepared from a synthesis mixture comprising fumed silica, sodium hydroxide, sodium aluminate, gallium nitrate and an aliphatic quaternary ammonium compound such as tetraethylammonium bromide.

As a result of the crystallisation process, the recovered zeolite contains within its microporous structure the organic structure directing agent used in the synthesis mixture.

The crystalline structure essentially wraps around the organic structure directing agent.

The more carbon rich an organic structure directing agent is the greater the carbon weight % will be present in a zeolite as-synthesised. In general, zeolites synthesised with organic structure directing agents which are aromatic compounds are likely to contain more carbon than zeolites prepared using aliphatic compounds as structure directing agents. It has been found that using basic nitrogen compounds as the organic structure directing agent a zeolite as-synthesised may contain about 4% or greater of carbon by weight, such as about 4% to about 5% carbon by weight. Examples of basic nitrogen compounds which typically provide about 4 wt % to about 5 wt % carbon in an as-synthesised zeolite include aliphatic quaternary ammonium compounds such as tetraethylammonium bromide, triethylmethylammonium bromide and 1,4-bis(triethylammonium) butane dibromide, aromatic quaternary ammonium compounds, for example benzyltrimethylammonium bromide and heterocyclic compounds containing amine functional groups such as morpholines, for example morpholine hydrobromide. The amount of carbon present in a zeolite may be determined by conventional elemental analysis.

Typically, zeolites prepared in the presence of organic structure directing agents are inactive as catalysts. This is believed to be due to the presence of the molecules of the structure direct agent in the pores of the zeolite which effectively hinder access to the active sites of the zeolite by reactant molecules. Thus, typically, as-synthesised zeolites are treated to remove organic structure directing agents from within their microporous channels. This is generally accomplished by a thermal treatment, such as calcination or heating, of an as-synthesised zeolite at elevated temperature, typically at temperatures of 500° C. and above. However, alternative methods may also be employed. For example, EP 1101735 describes a method for the removal of templating agents from synthetic zeolites by treating the zeolites with solvents in the vapour phase at low temperature. Removal of the organic structure directing agent from the zeolite increases its micropore volume and generally increases it to in excess of 0.01 ml/g.

Without wishing to be bound by theory, it is believed that in the carbonylation processes of the present invention, the active sites required for the chemical reaction between the reactant molecules, such as dimethyl ether and carbon monoxide, are accessible from the surface of the zeolite and hence access to the active sites through the porous channels of the zeolite by the reactant molecules is not necessary for the carbonylation reaction to take place. Surprisingly, the zeolite catalysts of the present invention demonstrate better selectivities to methyl acetate product with respect to the same zeolite from which the structure directing agent has been removed or substantially removed. In particular, the zeolite catalysts of the present invention demonstrate enhanced selectivities to methyl acetate product and decreased selectivities to by-products, such as hydrocarbons, particularly at or near to the start-up of the carbonylation process.

As described above, in the present invention, the organic structure directing agent used to prepare the zeolite is not subsequently removed from or not substantially removed from the zeolite as-synthesised, for example by a thermal treatment, such as calcination. The organic structure directing agent is retained or partially retained in the zeolites of the present invention so as to control the micropore volume of a zeolite to 0.01 ml/g or less, for example in the range 0.00 ml/g to 0.01 ml/g. Advantageously, therefore the zeolite catalysts of the present invention may be used in the carbonylation processes of the present invention as-synthesised or uncalcined.

In some or all embodiments of the present invention, the zeolite as-synthesised has a micropore volume in the range 0.00 ml/g to 0.01 ml/g and a carbon content of 4 wt % or greater, for example about 4 wt % to about 5 wt % carbon.

To the extent desired, cations in the zeolite as-synthesised, such as alkali or alkaline earth metal cations, can be replaced in accordance with techniques well-known in the art, at least in part, by ion-exchange with other cations. Preferred replacing cations include ammonium ions.

Suitably, in the present invention, the zeolite of micropore volume of 0.00 ml/g to 0.01 ml/g is utilised in an ion-exchanged form of the zeolite as-synthesised, such as an ammonium form or hydrogen form of the zeolite. Suitable examples include ion-exchanged forms of mordenite, such as an ammonium form mordenite or a hydrogen form mordenite.

Ion exchange may be carried out one or more times by contacting an as-synthesised zeolite with an aqueous solution of replacing cations, such as ammonium ions. In general, ion exchange is conducted at temperatures in the range 25 to 100° C. for a suitable time interval, for example 1 to 6 hours. The degree of the ion-exchange can be varied by changing the time of the contact, concentration of the replacing cation solution and temperature.

Suitable sources of ammonium cations include ammonium salts, for example ammonium nitrate or ammonium chloride.

Following contact with an aqueous salt solution of replacing cations, the zeolite may be washed with water and dried to produce a dry zeolite having the replacing cations occupying, for example the alkali/alkaline earth metal sites. Suitably, drying is conducted at low temperatures to avoid or at least mitigate significant removal of the organic structure directing agent from the zeolite micropores. Drying temperatures below 150° C. are therefore preferred, for example from 60° C. to 120° C.

As-synthesised zeolites in ammonium form may be employed to catalyse the carbonylation of dimethyl ether with carbon monoxide to produce methyl acetate. It is not necessary to blend an as-synthesised zeolite with a binder material. Thus, the present invention provides a simpler, and hence a more cost effective catalyst synthesis procedure.

As-synthesised zeolites are fine crystalline powders. Thus, it may be desired to increase the mechanical strength of the zeolite, by forming the zeolite into shaped particles, such as extrudates, pellets or beads. Processes for forming zeolites into shaped particles are well-known in the art and may be accomplished by forming a gel or paste of the zeolite powder with the addition of a suitable binder material and then extruding the gel or paste into the desired shape and then dried. Zeolite powders may also be formed into particles without the use of a binder.

Conveniently, a zeolite as-synthesised may be composited with a binder, for example an inorganic oxide or a clay. Preferred binder materials include aluminas, alumina-silicates and silicas, for example boehemite type alumina. However other inorganic oxides such as titanias, zirconias and magnesias may also be used. Suitable clays include bentonite and kieselguhr.

The relative proportions of a zeolite and the binder may vary widely but suitably, the zeolite may be present in the final catalyst in an amount of 10% to 90% by weight of the catalyst, preferably in an amount of 10% to 65% by weight of the catalyst.

The composited zeolite-binder mixture can be extruded to form the desired type of catalyst particle and optionally subjected to a thermal treatment to cure the binder and improve the catalyst strength and attrition resistance.

Thermal treatment, such as calcination of a zeolite composite is conducted so as to retain sufficient organic structure directing agent within the zeolite such that the micropore volume of the zeolite is maintained at 0.01 ml/g or less.

The thermal conditions to which a composited zeolite may be subjected are preferably controlled so as to reduce and/or eliminate exposure to temperatures above about 500° C. for a prolonged period of time. Suitable calcination conditions include temperatures ranging from 300° C. to 500° C., preferably from 350° C. to 450° C.

The catalyst may be calcined in the presence of an inert atmosphere, such as nitrogen or helium, or an oxidising atmosphere such as oxygen or air. Preferably, calcination of the composited zeolite is carried out in air, such as in static air.

The duration of the calcination may be, for example from about 10 minutes to 10 hours.

Calcination may be controlled such that the temperature is increased in a controlled manner to the final calcining temperature. Careful control of the increase in temperature prevents or at least minimises local overheating of the zeolite. Controlled calcination to the desired calcining temperature may be effected by applying slow ramp rates, such as less than 10° C./min, for example ramp rates from 1° C./min to 5° C./min.

The extent of removal of an organic structure directing agent from a zeolite can be determined by a comparison of the carbon content of the zeolite pre- and post-thermal treatment. Elemental analysis of the carbon content of a zeolite may be carried out by conventional methods, such as by combusting a known weight of the zeolite in air, measuring the amount of carbon dioxide produced from the combustion and calculating the weight % of carbon in the zeolite from the amount of produced carbon dioxide.

After a zeolite composite has been calcined, cations in the zeolite, such as alkali or alkaline earth metal cations, can be replaced in accordance with techniques well-known in the art and as described hereinabove, at least in part, by ion-exchange with other cations. Preferred replacing cations include ammonium ions.

In a further embodiment of the present invention, the zeolite having a micropore volume of less than 0.01 ml/g is a mordenite in ammonium form, composited with at least one inorganic oxide binder selected from aluminas, silicas and alumina-silicates, and in particular, the mordenite composite is a mordenite composite which contains gallium as a mordenite framework element.

Zeolites of the present invention when used as catalysts in the carbonylation of dimethyl ether with carbon monoxide exhibit improved performance, particularly during the induction period of the carbonylation reaction, compared to catalysts of the prior art.

The present invention thus further provides a process for producing methyl acetate by contacting dimethyl ether with carbon monoxide under carbonylation conditions in the presence of a catalyst of the present invention which catalyst comprises a zeolite of micropore volume of 0.01 ml/g or less.

Carbonylation processes to methyl acetate may be carried out by contacting dimethyl ether and carbon monoxide under carbonylation conditions in the presence of the zeolite catalysts of the present invention.

Dimethyl ether employed in the carbonylation process may be substantially pure dimethyl ether. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. In the present invention, the dimethyl ether may comprise small amounts of methanol provided that the amount of methanol is not so great as to inhibit the production of methyl acetate reaction product. Suitably, the dimethyl ether may contain 5 wt % or less, such as 1 wt % or less of methanol.

Diluents may be included in the dimethyl ether. Examples of suitable diluents include nitrogen, argon and helium.

Suitably, the concentration of dimethyl ether is in the range of from 0.1 to 20 mol %, such as 1.5 mol % to 15 mol % based on the total components of the gaseous feeds to the carbonylation reaction.

Preferably, dimethyl ether is utilised in the carbonylation process in the vapour phase.

The carbonylation process may be carried out in the presence of hydrogen.

The carbon monoxide and hydrogen gases may be substantially pure, for example, carbon monoxide and hydrogen typically provided by suppliers of industrial gases, or they may contain low levels of impurities that do not interfere with the carbonylation reaction, such as methane and carbon dioxide.

Conveniently, synthesis gas may be used as the source of carbon monoxide for the carbonylation process. Synthesis gas is a mixture of primarily carbon monoxide and hydrogen in varying amounts but it may also comprise small amounts of carbon dioxide and inert gases and is commercially available. Conventional processes for the production of synthesis gas include conversion reactions of hydrocarbon sources such as steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process may include the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

The synthesis gas used in the present carbonylation process may also comprise one or more of carbon dioxide and inert gases.

The carbonylation process may also be conducted in the presence of a diluent. Examples of suitable diluents include the inert gases, such as nitrogen, argon and helium.

On contact of the carbon monoxide and dimethyl ether with the zeolite catalyst under carbonylation reaction conditions, the carbonylation reaction is initiated and methyl acetate is produced as a reaction product. Hydrogen is largely unconsumed in the carbonylation process.

The carbonylation process may be conducted with carbon monoxide and hydrogen present in a variety of molar ratios, including equimolar. Suitably, the carbon monoxide to hydrogen molar ratio is in the range 1:3 to 15:1, for example 1:2 to 10:1, such as 1:2 to 4:1.

As water can inhibit the carbonylation of dimethyl ether to produce methyl acetate the carbonylation process is preferably carried out under substantially anhydrous conditions. Suitably therefore, to limit the presence of water in the carbonylation reaction, all reactants, including dimethyl ether, and carbon monoxide, and the catalyst are dried prior to their use in the carbonylation process. Suitably, in the carbonylation process water is present at a concentration of less than 1 mol %, based on the total gaseous feed to the carbonylation process, preferably less than 0.5 mol %, more preferably less than 0.2 mol %, and most preferably less than 0.1 mol %

Suitably, the carbonylation process is carried out at a temperature of from about 200° C. to about 350° C., for example of from about 240° C. to about 320° C., such as from about 260° C. to 300° C.

The carbonylation process may be carried out at a total pressure of from 1 to 100 barg, such as from 10 to 100 barg, for example from 20 to 80 barg, for instance 60 to 70 barg.

Desirably, the carbonylation process is carried out at a temperature of from about 240° C. to about 320° C., such as 260° C. to 300° C. and at a total pressure of from 20 to 80 barg, for example 60 to 70 barg.

Suitably, the carbonylation process is carried out at a total gas hourly space velocity (GHSV) of from about 500 to about 40,000 $h^{-1}$, for example of from about 2000 to about 10,000 $h^{-1}$.

Preferably, the carbonylation process is carried out substantially in the absence of halides, such as iodide. By the term 'substantially' is meant that the total halide, for example, iodide content of the gaseous feeds to the process and the catalyst is less than 500 ppm, preferably less than 100 ppm.

If desired, the dimethyl ether, carbon monoxide and if present, hydrogen may be contacted with a guard bed immediately before a bed of catalyst so as to remove impurities therefrom. Suitable guard beds include alumina.

Desirably, the carbonylation process is carried out as a vapour phase process, for example as a fixed bed process. Where the carbonylation process is operated as a vapour phase process, the feedstock(s), prior to entering a reaction zone, may be in the liquid phase. However, prior to contact with the catalyst, it may be desired to volatilise liquid phase components, for example by use of a pre-heater.

The carbonylation process may be carried out in a reaction zone by passing a gaseous feed of dimethyl ether, carbon monoxide and, if used hydrogen, through one or more fixed beds of the catalyst maintained at the desired reaction temperature. It is, of course understood that a reaction zone may be one or more separate reactors with suitable means therebetween to assure that the desired reaction temperature is maintained at the entrance to each reactor.

Prior to use, the catalyst may be activated, for example by heating the catalyst to the desired reaction temperature, and over any desired period of time, under one or more of carbon monoxide, hydrogen and inert gases such as nitrogen and helium.

The carbonylation process produces methyl acetate as the principal reaction product. The reaction product may further comprise additional components such as one or more of acetic acid, unreacted dimethyl ether, unreacted carbon monoxide and hydrogen. At least some of the methyl acetate may be converted to acetic acid by processes known in the art, such as by a hydrolysis process.

Suitably, the carbonylation process reaction product comprising methyl acetate is removed from a reaction zone in the form of a vapour. Methyl acetate may be recovered from the reaction product by any suitable means such as by condensing the vapour to a liquid fraction comprising the methyl acetate and a non-condensable gas fraction. The gas and liquid fractions may then be separated using known means such as knock-out drums or tangential inlet drums.

The methyl acetate recovered from the process reaction product may be sold as such or it may be utilised in downstream chemical processes. For instance, some or all of the recovered methyl acetate may be converted to acetic acid, for example by a hydrolysis process. Hydrolysis processes are known in the art, and include, for example reactive distillation in the presence of an acidic catalyst.

The process may be operated as a continuous or a batch process, preferably as a continuous process.

The invention is now illustrated with reference to the following non-limiting Examples.

EXAMPLE 1

Catalyst Preparation
Catalyst A (not in Accordance with the Invention)

Ga—Al H-mordenite was prepared in a 4 liter stainless steel autoclave under hydrothermal conditions from a synthesis mixture comprising sodium hydroxide, silica, sodium aluminate, gallium nitrate and tetraethyl ammonium bromide structure directing agent.

133.6 g $SiO_2$ (fumed silica) was added to 40.5 g NaOH dissolved in 1080 g of water and stirred for 1 hour. An aqueous solution of tetraethyl ammonium bromide (56.8 g dissolved in 180 g water) was added to the stirred $SiO_2$/NaOH/water mixture and stirred for 1 hour. An aqueous $Ga(NO_3)_3$ solution (36.12 g of $Ga(NO_3)_3$ hydrate, ex Aldrich dissolved in 210 g water) was added to the $SiO_2$/NaOH/water/tetraethylammonium bromide mixture and stirred for 30 minutes. An aqueous sodium aluminate solution (3 g of $NaAlO_2$ dissolved in 210 g water) was added to the $SiO_2$/NaOH/water/tetraethylammonium bromide/$Ga(NO_3)_3$ mixture and stirred for an hour. The resulting mixture was then transferred to a 4 liter stainless steel autoclave and hydrothermally treated for 14 days by maintaining it at a temperature of 150° C. under stirring at a speed of 200 rpm. The resulting precipitate was filtered, washed with deionised water and dried at 110° C. in an air oven. Elemental analysis of the dried zeolite showed it to contain about 5 weight % carbon. The dried zeolite was calcined at 550° C. for 12 hours under an atmosphere of static air to remove the organic structure directing agent. The calcined zeolite was converted to the ammonium form by three successive ion-exchanges in 1M $NH_4NO_3$ (aqueous) at 80° C. for 1 hour. The ammonium-exchanged zeolite was washed and filtered using deionised water, dried in an oven at 110° C. and then calcined in static air at 500° C. for 3 hours to obtain Ga—Al H-mordenite.

The zeolite was compacted at 12 tonnes in a 32 mm die set using a pneumatic press, and crushed and sieved to a particle size fraction of 100 to 160 microns.

Elemental analysis of Catalyst A showed it to contain less than 0.1 weight % carbon.

Catalyst B

Catalyst B was prepared by repeating the preparation of Catalyst A up to calcining of the zeolite at 550° C. This calcining step was omitted in the preparation of Catalyst B so as to retain the organic structure directing agent within the zeolite pores. The preparation was continued as follows. 4 g of dried as-synthesised zeolite was converted to the ammonium form by three successive ion-exchanges in 1M $NH_4NO_3$ (aqueous) at 80° C. for 1 hour. The ammonium-exchanged zeolite was washed and filtered using deionised water and then dried in an oven at 110° C. to obtain Ga—Al $NH_4$-mordenite. This zeolite was compacted at 12 tonnes in a 32 min die set using a pneumatic press, and crushed and sieved to a particle size fraction of 100 to 160 microns.

Elemental analysis of Catalyst B showed it to contain 4.9 weight % carbon indicating that >99% of the organic structure directing agent was present within its structure.

Catalyst Characterisation

The physiochemical properties of Catalysts A and B were determined using $N_2$ adsorption carried out at 77K in a Micromeritics Tristar 3000 apparatus equipped with Tristar 3000 v6.01 software for data analysis. Prior to analysis, samples of the Catalysts were degassed under vacuum at 60° C. for 30 minutes and then at 120° C. for 16 hours.

BET surface area ($S_{BET}$) was derived from data points in the relative pressure range of $p/p_0$=0.01-0.05 based on a published model [S. Brunauer, P. H. Emmett, E. Teller, J. Am. Chem. Soc. 60 (1938) 309].

The t-plot method was used to determine the micropore volume ($V_{microp}$) and external surface area ($S_{Ext}$) using a fitted thickness range of 0.35-0.5 nm [B. C. Lippens, J. H. de Boer, J. Catal. 4 (1965) 319-323].

The mesopore volume ($V_{mesop}$) was calculated by subtracting the micropore volume from the total pore volume (determined using the single point adsorption total pore volume; $p/p_0$>0.98).

Elemental analysis for carbon content of a zeolite as-synthesised was conducted by combustion using an Exeter Analytical CE440 CHN elemental analyser.

The physiochemical properties of Catalysts A and B are given in Table 1 below.

TABLE 1

| | $S_{BET}$ (m$^2$/g) | $S_{Ext}$ (m$^2$/g) | $V_{microp}$ (ml/g) | $V_{mesop}$ (ml/g) | Carbon (% wt) |
|---|---|---|---|---|---|
| Catalyst A | 420 | 39 | 0.14 | 0.06 | <0.1 |
| Catalyst B | 29 | 20 | 0.00 | 0.07 | 4.9 |

Carbonylation Reaction

Each of Catalysts A and B were used to catalyse the carbonylation of dimethyl ether with carbon monoxide as follows. The carbonylation reactions were carried out in a pressure flow reactor unit consisting of 16 identical parallel isothermal co-current tubular reactors of the type described in, for example WO2006107187. 100 micro liters (0.07 g) of the catalyst was loaded onto a metal sinter (20 micrometers pore size) within the reactor. 100 micro liters of gamma alumina was placed on top of the catalyst and the remainder of the reactor was filled with carborundum. The catalyst was activated by heating it at atmospheric pressure to a temperature of 300° C. under a gaseous feed of carbon monoxide, hydrogen and helium in a molar ratio of 1:2:0.1 at a gas flow rate of 6.1 ml/min. The reactor was then pressurised to 60 barg and left to equilibrate for two hours at which point catalyst activation was considered complete and the gaseous feed was replaced by a carbonylation gas feed comprising 29 mol % carbon monoxide, 58.2 mol % hydrogen, 2.8 mol % He, 5 mol % $CO_2$ and 5 mol % dimethyl ether at a gas flow rate of 6.7 ml/min. The carbonylation reaction was allowed to continue under these conditions for 188 hours.

The exit stream from the reactor was passed at periodic intervals to an Interscience Trace gas chromatograph equipped with one flame ionisation detector (FID) having a Rtx-1,1u (20 m*0.32 mm) column and a Rtx-wax, 0.25u (2 m*0.32 mm) column and two thermal conductivity detectors (TCD); a first TCD equipped with a Carboxen 1010 (2 m*0.32 mm) column and a Carboxen 1010 (28 m*0.32 mm) column and a second TCD equipped with a Poraplot U (2 m*0.32 mm) column and a Poraplot Q (12 m*0.32 mm) column.

Table 2 below shows the impact of using a zeolite in accordance with the present invention on the space time yields (STY) to methyl acetate (MeOAc), acetic acid (AcOH) and $C_1$-$C_3$ hydrocarbons and selectivity to acetyls products.

TABLE 2

| Catalyst | Reaction time/ hours | STY MeOAc g kg$^{-1}$ h$^{-1}$ | STY AcOH g kg$^{-1}$ h$^{-1}$ | STY $C_1$-$C_3$ hydrocarbons g kg$^{-1}$ h$^{-1}$ | Selectivity % |
|---|---|---|---|---|---|
| A | 2.6 | 6 | 239 | 85 | 32.3 |
| B | 3.0 | 496 | 23 | 2 | 96.4 |
| A | 9.3 | 264 | 277 | 34 | 67.3 |
| B | 9.8 | 922 | 72 | 6 | 94.2 |
| A | 175.6 | 783 | 47 | 5 | 95.4 |
| B | 176.1 | 797 | 41 | 3 | 96.8 |

Catalyst B becomes highly selective for making acetyls products early in the reaction and the product is predominantly methyl acetate. In contrast, at a similar point in time, Catalyst A produces considerable amounts of hydrocarbon by-products and the product is predominantly acetic acid.

EXAMPLE 2

Preparation of Catalyst C 133.35 g $SiO_2$ (Cab-osil M5, fumed silica) was dispersed in 900 g water. An aqueous solution of tetraethyl ammonium bromide (56.82 g dissolved in 180 g water) was added to the silica dispersion and thoroughly mixed for 1 hour. After 1 hour an aqueous NaOH solution (40.71 g dissolved in 180 g water) was added to the mixture and thoroughly stirred for 90 minutes. After 90 minutes an aqueous $NaAlO_2$ solution (17.51 g of $NaAlO_2$ (Fischer Scientific GP grade) dissolved in 210 g $H_2O$) was added to the stirred mixture which was then stirred for a further 1 hour before being transferred to a 4 liter stainless steel autoclave where it was hydrothermally treated for a period of 3.5 days under conditions of 170° C. and a stirring speed of 550 rpm. After 3.5 days zeolite crystals had formed which were separated from the mother liquor by filtration and then washed with deionised water and dried at 90° C. in an air oven. 10 g of the dried zeolite was subjected to an ammonium exchange procedure by treating it with an aqueous solution of $NH_4NO_3$ (100 mL, 1 M), warmed to 80° C. and the mixture stirred at this temperature for 1 hour. The resultant suspension was filtered and the solid was washed with $NH_4NO_3$. This ammonium exchange procedure was repeated twice more. In the final filtration step the solid was washed with deionised water instead of $NH_4NO_3$ before the washed solid was dried in an oven at 90° C. for 24 hours. The dried solid was ammonium form mordenite.

Elemental analysis of Catalyst C showed it to contain 4.7 weight % carbon indicating that >99% of the organic structure directing agent was present in its structure. The micropore volume ($V_{mesopore}$) of Catalyst C was determined to be 0.01 ml/g.

Carbonylation Reaction

Catalyst C was used to catalyse the carbonylation of dimethyl ether with carbon monoxide as follows. The carbonylation reactions were carried out in a pressure flow reactor unit consisting of 64 identical parallel isothermal co-current tubular reactors of the type described in, for example WO2006107187. The reactors were arranged in 4 blocks of 16 reactors, each block having an independent temperature control. 100 micro liters of Catalyst C (pressed and sieved to 100-160 µm fraction) was loaded onto a metal sinter having a pore size of 20 micrometers within each reactor to provide a GHSV of 4000 h$^{-1}$. The catalyst was activated by heating it at atmospheric pressure to a temperature of 100° C. under an inert gas stream at a flow rate of 6.7 mL/min. per reactor and held at this temperature for 1 hour. The reactors were then pressurised to 70 barg and allowed to equilibrate for one hour at which point catalyst activation was considered complete. The reactors were heated to a temperature of 260° C. and the inert gas stream was replaced by a carbonylation reaction gas feed comprising 43.5 mol % carbon monoxide, 43.5 mol % hydrogen, 6 mol % dimethyl ether, 5 mol % $N_2$ and 2 mol % He for a period of 2 hours. After 2 hours the composition of the gas feed was changed to 43.5 mol % carbon monoxide, 43.5 mol % hydrogen, 10 mol % dimethyl ether, 1 mol % $N_2$ and 2 mol % He for a period of 22 hours. After 22 hours, the composition of the gas feed was changed to 29 mol % carbon monoxide, 58 mol % hydrogen, 10 mol % dimethyl ether, 1 mol % $N_2$ and 2 mol % He for a period of 24 hours after which time the temperature was increased from 260° C. to 280° C. The carbonylation reaction was allowed to continue under these conditions for about 10 days.

The exit stream from a reactor was analysed by passing it to two Interscience Trace gas chromatographs. One gas chromatograph was equipped with one thermal conductivity detector (TCD) having a Molsieve 5A (25 m*0.32 mm) column and one flame ionisation detector (FID) having a DB 624 (28*0.25 mm) column. The second gas chromatograph was equipped with one TCD detector having a Carboxen 1010 (28 m*0.32 mm) column and two FID detectors; a first FID was equipped with a Wax FFAP (18 m*0.25 mm) column and a second FID was equipped with a Gaspro (20 m*25 mm) column.

At 280° C., the average space time yields were: methyl acetate 465 g/l/h; acetic acid 9.9 g/l/h; $C_1$-$C_3$ hydrocarbons 1.15 g/l/h and the average selectivity to methyl acetate was 96.9%.

The invention claimed is:

1. A carbonylation process for producing methyl acetate comprising contacting dimethyl ether and carbon monoxide under carbonylation conditions in the presence of a catalyst which catalyst comprises a zeolite of micropore volume of 0.01 ml/g and which zeolite is an as-synthesised organic structure directing agent-containing zeolite and contains at least one channel which is defined by an 8-member ring.

2. A process according to claim 1 wherein the carbonylation process is conducted in the presence of hydrogen.

3. A process according to claim 2 wherein the carbon monoxide to hydrogen molar ratio is in the range 1:3 to 15:1.

4. A process according to claim 2 wherein the source of carbon monoxide is a synthesis gas.

5. A process according to claim 1 wherein water is present at a concentration of less than 1 mol %, based on the total gaseous feed to the carbonylation process.

6. A process according to claim 1 which process is carried out at a temperature of from 240° C. to 320° C. and at a total pressure of from 20 to 80 barg.

7. A process according to claim 1 wherein the process is conducted as a vapour phase process.

8. A process according to claim 1 wherein methyl acetate is recovered from the carbonylation process and at least some of the recovered methyl acetate is converted to acetic acid.

* * * * *